(12) United States Patent
Acar et al.

(10) Patent No.: US 12,318,456 B2
(45) Date of Patent: Jun. 3, 2025

(54) THERAPEUTIC NANOPARTICLES CONTAINING ARGONAUTE FOR MICRORNA DELIVERY AND COMPOSITIONS AND METHODS USING SAME

(71) Applicants: KOC UNIVERSITESI, Istanbul (TR); SABANCI UNIVERSITESI, Istanbul (TR); SABANCI UNIVERSITESI NANOTEKNOLOJI ARAŞTIRMA VE UYGULAMA MERKEZI, Istanbul (TR)

(72) Inventors: Havva Yagci Acar, Istanbul (TR); Devrim Gozuacik, Istanbul (TR); Ali Kosar, Istanbul (TR); Ozlem Unal, Istanbul (TR); Muhammed Kocak, Istanbul (TR); Yunus Akkoc, Istanbul (TR); Merve Zuvin, Istanbul (TR)

(73) Assignees: KOC UNIVERSITESI, Istanbul (TR); SABANCI UNIVERSITESI, Istanbul (TR); SABANCI UNIVERSITESI NANOTEKNOLOJI ARASTIRMA VE UYGULAMA MERKEZI, Istanbul (TR)

( * ) Notice: Subject to any disclaimer, the term of this patent is extended or adjusted under 35 U.S.C. 154(b) by 946 days.

(21) Appl. No.: 16/978,067

(22) PCT Filed: Mar. 10, 2018

(86) PCT No.: PCT/TR2018/050094
§ 371 (c)(1),
(2) Date: Sep. 3, 2020

(87) PCT Pub. No.: WO2019/177550
PCT Pub. Date: Sep. 19, 2019

(65) Prior Publication Data
US 2021/0023239 A1    Jan. 28, 2021

(51) Int. Cl.
| | | |
|---|---|---|
| A61K 47/68 | (2017.01) |
| A61K 33/243 | (2019.01) |
| A61K 41/00 | (2020.01) |
| A61K 47/54 | (2017.01) |
| A61K 47/69 | (2017.01) |
| B82Y 5/00 | (2011.01) |

(52) U.S. Cl.
CPC ........ *A61K 47/6855* (2017.08); *A61K 33/243* (2019.01); *A61K 41/0052* (2013.01); *A61K 47/549* (2017.08); *A61K 47/6929* (2017.08); *B82Y 5/00* (2013.01)

(58) Field of Classification Search
CPC ............ A61K 47/6855; A61K 47/6929; A61K 47/549; A61K 33/243; A61K 41/0052
See application file for complete search history.

(56) References Cited

U.S. PATENT DOCUMENTS

| | | | |
|---|---|---|---|
| 2014/0050670 A1* | 2/2014 | Iyer .................. | A61P 35/00 |
| | | | 435/375 |
| 2016/0152987 A1* | 6/2016 | Saltzman ............ | A61K 9/0034 |
| | | | 435/375 |
| 2016/0369272 A1* | 12/2016 | Hofman .............. | C12N 15/111 |
| 2017/0002424 A1 | 1/2017 | Lozano Castro et al. | |

FOREIGN PATENT DOCUMENTS

| | | |
|---|---|---|
| CN | 103849652 B | 6/2016 |
| EP | 1259263 B1 | 9/2004 |
| EP | 2622075 B1 | 3/2016 |
| WO | 2013016126 A1 | 1/2013 |
| WO | 2015138636 A1 | 9/2015 |
| WO | WO-2018013957 A1 * | 1/2018 ............ A61K 41/00 |

OTHER PUBLICATIONS

Xu et al. "Bleomycin Loaded Magnetite Nanoparticles Functionalized by Polyacrylic Acid as a New Antitumoral Drug Delivery System", Biomed Res Int. 2013:2013:462589 (Year: 2013).*
Mark A. Kay, State-of-the-art gene-based therapies: the road ahead, Nature Reviews Genetics, May 2011, pp. 316-328, vol. 12.
Beverly L. Davidson et al., Current prospects for RNA interference-based therapies, Nature Reviews Genetics, May 2011, pp. 329-340, vol. 12.
Daniel H. Kim et al., Strategies for silencing human disease using RNA interference, Nature Reviews Genetics, Mar. 2007, pp. 173-184, vol. 8.
Jacek Krol et al., The widespread regulation of microRNA biogenesis, function and decay, Nature Reviews Genetics AOP, Jul. 27, 2010, pp. 1-14.

(Continued)

*Primary Examiner* — Daniel E Kolker
*Assistant Examiner* — Peter Johansen
(74) *Attorney, Agent, or Firm* — Bayramoglu Law Offices LLC

(57) ABSTRACT

The present invention relates to oligonucleotide carriers for oligonucleotide delivery to a subject to provide gene therapy. More particularly, the present invention relates to therapeutic nanoparticles for microRNA (miRNA) delivery to a subject. More particularly, the present invention relates to therapeutic nanoparticles wherein miRNA is bindable to biocompatible nanoparticles using natural gene carrier Argonaute (AGO) protein or a variant thereof. Optionally, therapeutic nanoparticles of the present invention additionally contain targeting moieties for targeting therapeutic nanoparticles to cancer cells and/or chemotherapeutic agents. Optionally, biocompatible nanoparticles are trackable nanoparticles, such as superparamagnetic iron oxide nanoparticles (SPION), to provide multifunctional theranostics.

25 Claims, 5 Drawing Sheets
Specification includes a Sequence Listing.

(56) References Cited

OTHER PUBLICATIONS

Julia Hock et al., Protein family review, The Argonaute protein family, Genome Biology, 2008, pp. 1-8, vol. 9, Issue 2, Article 210.
Julia Winter et al., Argonaute proteins regulate microRNA stability: Increased microRNA abundance by Argonaute proteins is due to microRNA stabilization, RNA Biology, 2011, pp. 1149-1157, vol. 8, Issue 6.
Jenny KW Lam et al., siRNA versus miRNA as Therapeutics for Gene Silencing, Molecular Therapy-Nucleic Acids, 2015, pp. 1-20.
AG Bader et al., Developing therapeutic microRNAs for cancer, Gene Therapy, 2011, pp. 1121-1126, 18.
D. Gozuacik et al., Anticancer Use of Nanoparticles as Nucleic Acid Carriers, Journal of Biomedical Nanotechnology, 2014, pp. 1751-1783, vol. 10, No. 9.
Yan Wang et al., Nanoparticle-Based Delivery System for Application of siRNA In Vivo, Current Drug Metabolism, 2010, pp. 182-196, vol. 11, No. 2.
Jason D. Arroyo et al., Argonaute2 complexes carry a population of circulating microRNAs independent of vesicles in human plasma, PNAS, Mar. 22, 2011, pp. 5003-5008, vol. 108, No. 12.
Elad Elkayam et al., The Structure of Human Argonaute-2 in Complex with miR-20a, Cell 150, Jul. 6, 2012, pp. 100-110.
Andreas Boland et al., Crystal structure and ligand binding of the MID domain of a eukaryotic Argonaute protein, EMBO reports, 2010, pp. 522-527, vol. 11, No. 7.
Kumsal Ayse Tekirdag et al., MIR376 family and cancer, Histology and histopathology, Mar. 2016, pp. 1-37.
Jakob Lewin Rukov et al., Pharmaco-miR: linking microRNAs and drug effects, Briefings in Bioinformatics, Jan. 2013, pp. 648-659, vol. 15, No. 4.
Gozde Korkmaz et al., MIR376A Is a Regulator of Starvation-Induced Autophagy, Plos One, Dec. 2013, pp. 1-10, vol. 8, Issue 12.
André C Silva et al., Application of hyperthermia induced by superparamagnetic iron oxide nanoparticles in glioma treatment, International Journal of Nanomedicine, 2011, pp. 591-603, 6.
Jilie Kong et al., Fourier Transform Infrared Spectroscopic Analysis of Protein Secondary Structures, Acta Biochimica et Biophysica Sinica, 2007, pp. 549-559, vol. 39, No. 8.
Mehmet V. Yigit et al., Magnetic Nanoparticles for Cancer Diagnosis and Therapy, NIH Public Access Author Manuscript, Pharm Res., 2013, pp. 1-15.
M. Kocak et al., Spion Nanoparticles as a miRNA Delivery Vehicle in Breast Cancer, MolBiyoKon'17, 5th International Congress of the Molecular Biology Association of Turkey, Short Talk-14, Sep. 8-10, 2017, pp. 42, Bogazici University, Istanbul.
Jiahe Li et al., Structurally modulated codelivery of siRNA and Argonaute 2 for enhanced RNA interference, PNAS, 2018, pp. E2696-E2705, vol. 115, No. 12.
Shengqiang Xu et al., MiRNA extraction from cell-free biofluid using protein corona formed around carboxyl magnetic nanoparticles, ACS Biomaterials Science & Engineering, 2017, pp. 1-29.
Andreas Lingel et al., Nucleic acid 3'-end recognition by the Argonaute2 PAZ domain, Nature Structural & Molecular Biology, Jun. 2004, pp. 576-577, vol. 11, No. 6.
Nicole T. Schirle et al., Structural Basis for microRNA Targeting, NIH Public Access Author Manuscript, 2015, pp. 1-16.
Andrey Turchinovich et al., Distinct AGO1 and AGO2 associated miRNA profiles in human cells and blood plasma, RNA Biology, Aug. 2012, pp. 1066-1075, vol. 9, Issue 8.
Yanli Wang et al., Structure of the guide-strand-containing argonaute silencing complex, Nature, Nov. 13, 2008, pp. 209-213, vol. 456.

\* cited by examiner

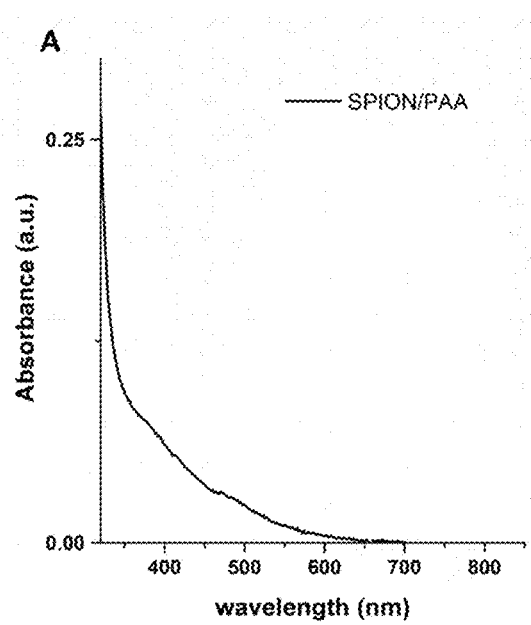
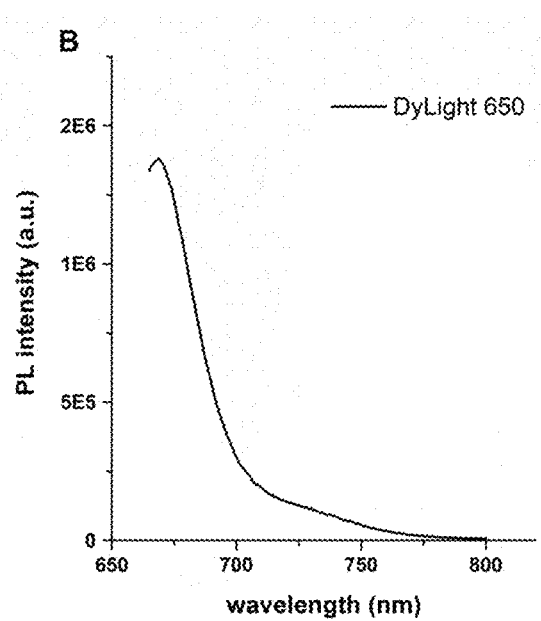
FIG. 2A  FIG. 2B
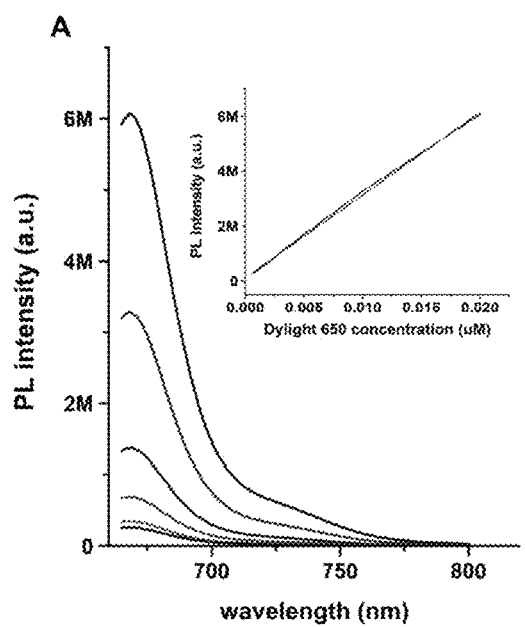
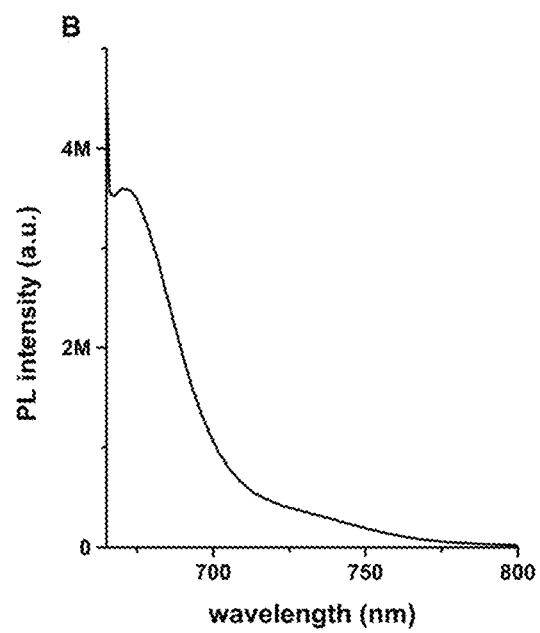
FIG. 3A  FIG. 3B

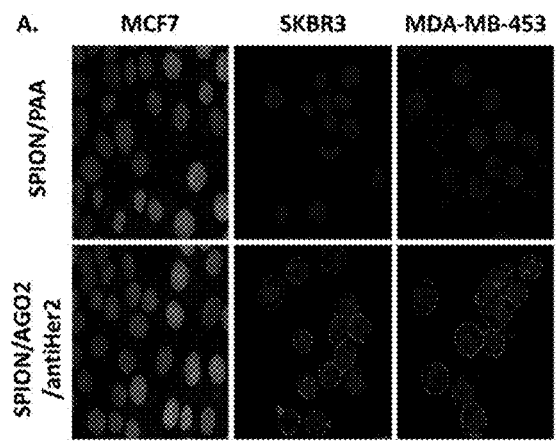
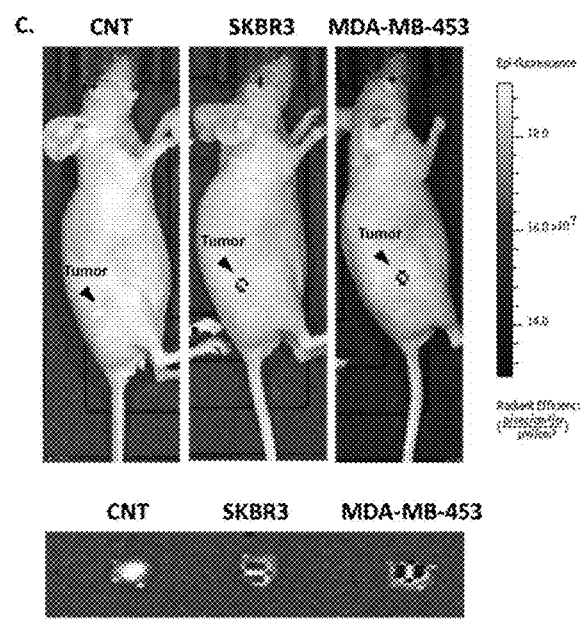
FIG. 8A
FIG. 8C
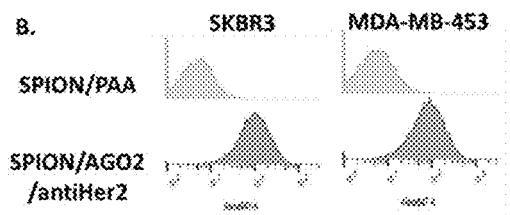
FIG. 8B
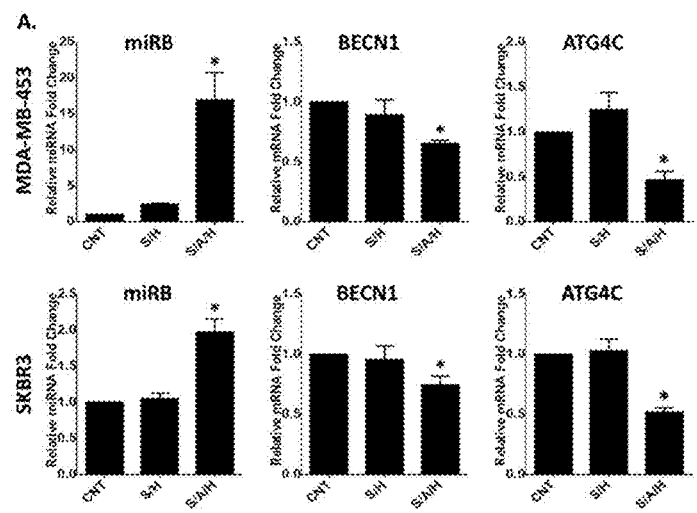
FIG. 9A
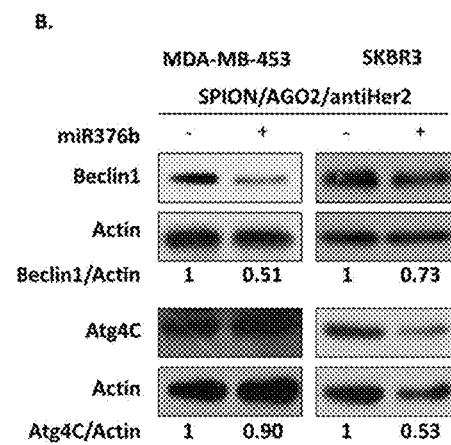
FIG. 9B

THERAPEUTIC NANOPARTICLES CONTAINING ARGONAUTE FOR MICRORNA DELIVERY AND COMPOSITIONS AND METHODS USING SAME

CROSS REFERENCE TO THE RELATED APPLICATIONS

This application is the national phase entry of International Application No. PCT/TR2018/050094, filed on Mar. 10, 2018, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBSA008-Sequence Listing-20200814.txt, dated Aug. 14, 2020 and is 4 kilobytes in size.

TECHNICAL FIELD

Broadly, the present invention relates to oligonucleotide carriers for oligonucleotide delivery to a subject. More particularly, the present invention relates to the development of therapeutic nanoparticles for microRNA (miRNA) delivery to a subject. More particularly, the present invention relates to therapeutic nanoparticles wherein miRNA is bound to pharmaceutically acceptable nanoparticles using natural gene carrier Argonaute-2 (AGO2) protein or a variant thereof.

BACKGROUND

Gene-based therapeutics can be broadly defined as a vector for nucleic acid delivery into cells with the intention of altering gene expression to prevent, halt or reverse a pathological process. Gene therapy can be carried out by three routes: gene addition, gene correction/alteration and gene knockdown, which are sometimes used in combination. Recently, new tools for modulating single genes or complex gene networks have renewed enthusiasm in gene-based therapeutics due to the discovery of small RNA-mediated gene regulation circuits and the ability to virtually eliminate a gene product using RNA interference (Kay. Nature Rev Genet. 2011. 12:316-328).

RNA interference (RNAi) is a natural cellular process that regulates gene expression and provides an innate defense mechanism against invading viruses and transposable elements (Davidson and McCray. Nature Rev Genet. 2011. 12:329-340). RNAi pathways are guided by endogenous non-coding RNAs that include small interfering RNAs (siRNAs) and microRNAs (miRNAs). RNAi effector molecules induce gene silencing in several ways: they direct sequence-specific cleavage of perfectly or imperfectly complementary mRNAs and translational repression (Kim and Rossi. Nature Rev Genet. 2007. 8:173-184). The regulation of gene expression by miRNA has been shown by RNA induced silencing complex (RISC) composing of primarily nearly a 22 nucleotide single strand RNA and a ribonucleoprotein, Argonaute (AGO).

Four different AGO protein subfamily members, AGO1, AGO2, AGO3 and AGO4, exist in mammalian systems. They have common domains in their structures which have special RNA binding motifs for binding miRNAs (Krol et al. Nature Rev Genet. 2010. 11:597-610). These domains are reported to protect small RNA from nucleases by blocking their access to the 3' and 5' sites of miRNAs (Höck and Meister. Genome Biol. 2008. 9:210). Each human AGO protein has the potential to stabilize and protect miRNA abundance and AGO proteins are reported to bind miRNAs in the human blood and stabilize them in the plasma (Winter and Diederichs. RNA Biol. 2011 8:1149-57; Turchinovich and Burwinkel. RNA Biol. 2012. 9:1066-1075).

However, only AGO2 protein is able to catalyze cleavage for target mRNA. In RISC, the RNA strand basically guides AGO2 to target mRNA using the base complementarity. If guide and target strands are complementary with each other, catalytically active site of AGO2 slices the mRNA to inhibit translation.

To elicit RNAi, the siRNA must be fully complementary to its target mRNA. By contrast, the target recognition of miRNA is more complex, as different binding sites and different degree of complementarity between the miRNA and the target RNA exist. As one miRNA strand can recognize an array of mRNAs, miRNA has the characteristic of having multiple targets. The disruption of miRNA functions contributes to the development of many diseases including cancers, neurodegenerative disorders and cardiovascular diseases (Lam et al. Mol Ther Nucleic Acids. 2015. 4: e252).

Both siRNAs and miRNAs have huge potential as therapeutic agents. They can overcome the major limitation of traditional small drug molecules, which can only target certain classes of proteins. siRNAs and miRNAs can down-regulate the expression of virtually all genes and their mRNA transcripts. Since many diseases result from the expression of undesired or mutated genes, or from overexpression of certain normal genes, the discovery of siRNA and miRNA opens up a whole new therapeutic approach for the treatment of diseases by targeting genes that are involved causally in the pathological process (Lam et al. Mol Ther Nucleic Acids. 2015. 4:e252).

Naturally occurring and synthetic miRNAs are essential tools for perturbing mRNA function. Synthetic miRNAs can be chemically modified to increase their stability and loading to RISC complex (Bader et al. Gene Ther. 2011. 18:1121-6). This can be achieved by terminal modifications on synthetic miRNAs such as sugar and phosphate modifications; 2'-O-methyl, phosphorothioate, boranophosphate or methylphosphonate backbone linkages, 2 sugar modifications such as 2'-fluoro, LNA (Locked nucleic acids), FANA (2'-deoxy-2'-Fluoro-beta-d-arabinonucleic acid), and 2'MOE (2'-O-methoxyethyl) modifications (Gozuacik et al. J Biomed Nanotechnol. 2014. 10:1751-83).

Patent document EP 2 622 075 (B1) discloses the use of miRNAs that are members of the hsa-miR-376 family or inhibitors of said miRNAs for the diagnosis, prophylaxis, treatment and follow-up during and after treatment of diseases involving autophagy abnormalities by acting on autophagy-related genes and proteins.

Patent document US 2017/002424 (A1) discloses methods for predicting the risk of recurrence of breast tumors using the expression signature of particular miRNAs (selected from among miR-149-5p, miR-10a-5p, miR-20b-5p, miR-30a-3p and miR-342-5p) in a sample of the tumor. A change in the expression level of at least one miRNA in the tumor with respect to the expression level in a control sample is indicative of a high risk of recurrence of the tumor.

As outlined above, miRNA-based therapies are highly attractive as a therapeutic approach; however, several hurdles must be overcome to successfully introduce them into the clinic. miRNA has a poor pharmacokinetic profile in vivo due to the susceptibility of RNA molecules to serum nucleases, renal clearance and non-targeted bio-distribution. In addition, the negative charges of RNAs impair their accessibility to the extracellular and intracellular target sites. All of these characteristics compromise their gene silencing efficacy (Wang et al. Current Drug Metabolism. 2010. 11:182-196).

To overcome these hurdles, various local or systemic miRNA delivery strategies have been developed. Especially systemic miRNA delivery has been intensely studied with viral and non-viral delivery approaches. Although viral entities show efficient transfection of miRNAs, they are immunogenic and mutagenic. Therefore, relatively non-toxic non-viral delivery agents are stronger candidates for miRNA delivery. Biocompatible formulations such as nanoparticles that are made of synthetic, natural cationic polymers or cationic species are being studied to potentially overcome extracellular and intracellular barriers and facilitate site-specific delivery, cellular uptake and intracellular target interactions of miRNA.

Patent document EP 1 259 263 (B1) discloses the complexation of RNA with optionally modified polyethylenimines (PEI) for stabilization and for cellular internalization of the complexed RNA in vitro and in vivo.

Patent document CN 103849652 (B) discloses a nano-carrier system for miRNA. The nano-carrier system consists of protamine sulfate, hyaluronic acid and the target miRNA, wherein the target miRNAs are miRNA mimics with a cancer inhibition function. Cationic protamine sulfate and anionic hyaluronic acid are combined through electrostatic interaction so as to form a nano carrier. miRNA is loaded into the nano carrier during the formation process, whereby miRNA is wrapped by protamine sulfate and hyaluronic acid to protect miRNA and prevent miRNA from being degraded by RNases.

Patent document WO 2013/016126 (A1) discloses therapeutic nanoparticles containing a polymer coating, such as dextran, and a nucleic acid that is covalently linked to the nanoparticle. Said nucleic acid contains a sequence complementary to a sequence within a miRNA related to cancer cell metastasis or anti-apoptotic activity in cancer cells (e.g., miR-10b) or a sequence within a mRNA encoding a pro-apoptotic protein.

However, in spite of the advantages of these delivery systems, miRNA delivery still suffers from the toxicity of the delivery vector, non-specific uptake and immune attacks which are directly caused by the positive charges on delivery agents. Therefore, biocompatibility and electronic charge of gene carrier systems have to be considered more comprehensively and natural alternatives have to be developed.

As mentioned above, recent studies have shown that mature miRNAs also exist in nuclease containing blood plasma and serum without any degradation. It has been suggested that AGO2 protein is responsible for the circulation and protection of majority of these extracellular miR-NAs in biological media (Arroyo et al. PNAS. 2011. 108: 5003-5008).

Patent document WO 2015/138636 (A1) discloses compositions, methods and kits for using AGO2 as a systemic carrier to deliver miRNAs to endothelial cells. The document also discloses compositions, methods and kits for inhibiting angiogenesis and/or treating a condition, such as brain vascular diseases and brain tumors, by using AGO2 as a systemic carrier to deliver miRNAs to endothelial cells. Said carrier system may also comprise anti-angiogenic drugs or chemotherapeutic agents to provide combination therapy. However, this document does not disclose features that allow greater specificity, such as targeting moieties, or features that impart diagnostic characteristics, such as fluorophores or magnetic entities for imaging applications, to the carrier design.

Thus, there is a need in the art for a robust miRNA carrier system that excludes the toxic effects of polycations as conventional gene carriers while providing targeting, tracking and diagnostic capabilities of nanoparticle based gene carrier systems. The present invention aims to fulfill this need by incorporating AGO protein into a diagnostic nanoparticle. Preferably, said diagnostic nanoparticle is a targetable and trackable diagnostic nanoparticle.

SUMMARY

The present invention proposes an oligonucleotide carrier, more particularly; the present invention proposes a therapeutic nanoparticle wherein oligonucleotides, specifically miRNA, are bindable to biocompatible nanoparticles using natural miRNA carrier AGO proteins or variants thereof as an oligonucleotide binding moiety.

The present invention proposes a biocompatible oligonucleotide carrier comprising AGO proteins and superparamagnetic iron oxide nanoparticles which provides tracking and diagnostic capability via MRI.

The present invention also proposes a biocompatible oligonucleotide carrier comprising AGO proteins, superparamagnetic iron oxide nanoparticles and a targeting moiety specific to a receptor overexpressed in target cell lines or tumors.

The present invention also proposes an oligonucleotide carrier comprising AGO proteins, superparamagnetic iron oxide nanoparticles, therapeutic miRNA and a targeting moiety as a potential source of combination therapy which may include hyperthermia and chemotherapy.

The present invention also proposes dual targeting of the said oligonucleotide carrier to a target site by targeting ligands bound to the carrier and by magnetic dragging in an external magnetic field.

The present invention provides an oligonucleotide carrier as provided by the characterizing features defined in claim 1.

The object of the invention is to provide an oligonucleotide carrier.

A further object of the invention is to provide an oligonucleotide carrier comprising AGO or a variant thereof conjugated to a pharmaceutically acceptable delivery agent. Preferably, said AGO protein or a variant thereof is an AGO2 protein or a variant thereof.

A further object of the invention is to provide an oligonucleotide carrier comprising multifunctional nanoparticles capable of delivering therapeutic miRNA and generating hyperthermia at the targeted tumors and generating signals detectable by MRI and/or fluorescent microscopes.

A further object of the invention is to provide an oligonucleotide carrier comprising multifunctional nanoparticles capable of delivering therapeutic miRNA to targeted tumors with greater specificity using targeting moieties, such as proteins, peptides, nucleic acids, small molecules or others.

A further object of the invention is to provide an oligonucleotide carrier comprising multifunctional nanoparticles capable of delivering therapeutic miRNA to targeted tumors with greater specificity using targeting moieties and an external magnetic field.

A further object of the invention is to provide a use of said oligonucleotide carriers for delivering oligonucleotides to a subject.

A further object of the invention is to provide a use of said oligonucleotide carriers in theranostic applications, such as cancer diagnosis and treatment.

A further object of invention is to provide a use of said oligonucleotide carriers to increase effects of chemotherapeutic agents.

BRIEF DESCRIPTION OF THE DRAWINGS

FIG. 2A demonstrates absorbance spectrum of SPION/PAA in PBS (0.08 mg/mL). FIG. 2B demonstrates PL spectrum of DyLight 650® in PBS (4 nM).

FIGS. 3A-B demonstrate antiHer2 concentration measurement by PL spectroscopy. FIG. 3A demonstrates PL spectra of DyLight 650® at decreasing concentrations ($2\times10^{-2}$, $1\times10^{-2}$, $4\times10^{-3}$, $2\times10^{-3}$, $1\times10^{-3}$, $5\times10^{-4}$ µM), $\lambda_{ex}$=655 nm, inset: Calibration curve of PL intensity vs concentration of DyLight 650®. FIG. 3B demonstrates PL spectrum of SPION/AGO2/antiHer2 ($\lambda_{ex}$655 nm, dilution factor=20).

FIG. 6A demonstrates the cytotoxic effect of miRNA-bound nanoparticles in combination with 5 µg cisplatin on cell viability of SKBR3 determined after 48 hours treatment. FIG. 6B. demonstrates the cytotoxic effect of miRNA-bound nanoparticles in combination with 5 µg cisplatin on cell viability of MDA-MB-453 cells determined after 48 hours treatment.

FIGS. 8A-C demonstrate targeting ability of SPION/AGO2/antiHer2 nanoparticles in vitro and in vivo. FIG. 8A demonstrates fluorescent microscopy images of non-Her2 overexpressed MCF7 and Her2 overexpressed breast cancer cells (SKBR3 and MDA-MB-453) after being treated with SPION/PAA or SPION/AGO2/antiHer2. Blue dye indicates the cell nucleus. Red photoluminescence of nanoparticles originates from the conjugated dye to SPION/AGO2/antiHer2. FIG. 8B demonstrates flow cytometry analysis of SKBR3 and MDA-MB-453 cells treated after SPION/PAA and SPION/AGO2/antiHer2. FIG. 8C demonstrates in vivo delivery of SPION/AGO2/antiHer2 nanoparticles targets the primary tumor in the breast cancer model. Live imaging of nude mice with MDA-MB-453 and SKBR3 breast tumors after 24 hours of intravenous SPION/AGO2/antiHer2 andor SPION/PAA nanoparticles injection. Ex vivo fluorescent images of tumors were shown. SPION/PAA particles were injected as control.

FIGS. 9A-B demonstrate miRNA transfection efficiency of SPION/AGO2/antiHer2 nanoparticles in MDA-MB-453 and SKBR3 cells. FIG. 9A demonstrates quantitative PCR (QPCR) analysis of miR376b level and its targets ATG4C and BECN1 mRNAs in untreated (CNT), SPION/antiHer2 (S/H) and SPION/AGO2/antiHer2 (S/A/H) treated MDA-MB-453 and SKBR3 cells. QPCR data was normalized using U6 small nuclear 1 (RNU6-1) mRNA for miR376b and GPADH for ATG4C and BECN1 mRNAs. FIG. 9B demonstrates immunoblots of SPION/AGO2/antiHer2 treated MDA-MB-453 and SKBR3 cells. miRNA unbound SPION/AGO2/antiHer2 nanoparticles were used as control. Actin protein was used as loading control. ImageJ densitometric analysis of Atg4C and Beclin1 immunoblots were marked as the number below each band which represents the ratio of the band intensity to the respective Actin band intensity.

DETAILED DESCRIPTION OF THE EMBODIMENTS

The present invention proposes an oligonucleotide carrier, more particularly; the present invention proposes a therapeutic nanoparticle wherein oligonucleotides are bindable to biocompatible nanoparticles using AGO proteins or variants thereof as a natural and nontoxic binding moiety. Preferably, said oligonucleotides are short RNA sequences taking part in the RNAi pathway as described above. More preferably, said oligonucleotides are miRNAs.

However, the skilled person can appreciate that a variant of an AGO protein can include, but are not limited to, wild-type AGO, recombinant AGO, those that include conservative amino acid mutations, SNP variants, splicing variants, degenerate variants, biologically active portions of a gene, and AGO fragments which possess a biological activity that is substantially similar to a biological activity of AGO. In accordance with the present invention, the AGO protein may be modified, for example, to facilitate or improve identification, expression, isolation, storage and/or administration, so long as such modifications do not reduce AGO's function to unacceptable level. In various embodiments, a variant of the AGO protein has at least 10%, 20%, 30%, 40%, 50%, 60%, 70%, 80%, 90%, or 95% of the function of a wild-type AGO protein.

In a preferred embodiment of the invention, said AGO proteins or variants thereof are chosen to be AGO2 proteins or variants thereof.

Figure 10:
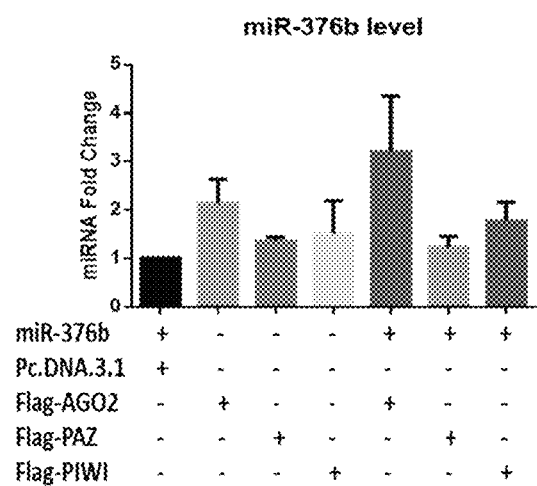
FIG. 10 demonstrates levels of exogenous and endogenous MIR376B in AGO2(aa860) and AGO2 fragments, PAZ(aa1-480) and PIWI(aa478-860), overexpressing HEK293T cells after immunoprecipitation of flag-tagged proteins with flag-beads were determined by Taqman QPCR.

The miRNA is anchored in AGO2 protein and makes several kinks and turns along the binding groove (Elkayam et al. Cell. 2012. 150:100-110). A binding pocket composed of residues from PAZ and PIWI domains as previously observed interacts with miRNA (Boland et al. EMBO Rep. 2010. 11:522-527; Lingel et al. Nat Struct Mol Biol. 2004. 11:576-577; Schirle et al. Science. 2014. 346:608-613; Wang et al. Nature. 2008. 456:209-213). To determine which domain of AGO2 protein have the key role in miRNA binding affinity, flag tagged AGO2 protein and its domains, PAZ and PIWI, were overexpressed in HEK293T cells in the presence or absence of miR-376b overexpression and they immunoprecipitated with flag beads. RNA isolation from the beads were showed that the domains have a partial role in miRNA binding, however, full length AGO2 protein has a greater affinity to bind miR-376b. It can be concluded that each domain of AGO2 protein is essential for the highest binding affinity (FIG. 10).

In a preferred embodiment of the invention, said AGO2 proteins or variants thereof are chosen to be full length AGO2 proteins or variants thereof. However, in some embodiments of the invention, AGO2 proteins or variants thereof may be fragments of AGO2 proteins having an acceptable level of miRNA binding ability compared to the function of a wild-type AGO2 protein.

The therapeutic nanoparticle of invention may be any biocompatible and pharmaceutically acceptable nanoparticle known in the art, including but not limited to lipid nanoparticles, polymeric nanoparticles, inorganic nanoparticles including but not limited to, magnetic nanoparticles, quantum dots, gold nanoparticles, silver nanoparticles, silica nanoparticles and the like.

In a preferred embodiment of the invention, said therapeutic nanoparticle comprises biocompatible, MRI active magnetic nanoparticles (superparamagnetic iron oxide nanoparticles, SPIONs) and a natural protein AGO2 as a miRNA binding moiety. Hence, SPION conjugated AGO2 nanoparticles can bind and deliver miRNA to a target and can be tracked via MRI. In addition to delivering miRNA and tracking of nanoparticles by MRI, the SPION component of the composition can also induce thermal ablation of the cells as an adjuvant therapy.

The therapeutic nanoparticle of invention is covalently conjugated to AGO2 protein. In a preferred embodiment of the invention, said therapeutic nanoparticle of invention is covalently conjugated to AGO2 protein by an amide bond. However, the person skilled in the art would appreciate that other bioconjugation methods can be utilized.

In a preferred embodiment of the invention, SPION with polyacrylic acid (PAA) coating was produced for covalent conjugation of AGO2 protein to SPION. PAA coating provides a colloidally stable, anionic SPION in aqueous media which is biocompatible and have reactive —COOH groups available for protein conjugation via methods known to a skilled person. However, many different functional SPIONs may be used, such as but not limited to SPIONs coated with organic molecules or polymers or the mixture of the two providing reactive groups on SPION such as carboxylic acid, amine, epoxide, thiol, azide, etc. SPIONs coated with functional silica shell with similar functionalities on the surface may also be utilized. In the examples provided below, SPION/PAA nanoparticles were produced in a small size regime which allowed synthesis of the preferred embodiments in a small size regime as well.

In a preferred embodiment of the invention, said miRNA is chosen from the MIR376 family. In recent studies, dysregulation of MIR376 family members was observed in various carcinomas and sarcomas, solid tumors and leukemia. Recent studies have also shown that the expression levels of MIR376 family members correlated with tumor grade, invasiveness, metastasis and/or chemotherapy responsiveness. Therefore, it is clear that miRNAs belonging to this family have huge potential as novel cancer biomarkers. Additionally, the MIR376 family was shown to regulate autophagy in cancer cells. Autophagy plays a critical role in several human diseases including cancer and autophagy abnormalities were observed during cancer formation and progression. As a result, MIR376 family levels are determined to be a critical factor for cancer cell survival and growth (Tekirdag et al. Histol Histopathol. 2016. 31:841-855). However, the person skilled in the art would appreciate that any miRNA sequence known in the art or a combination thereof may be used depending on the desired therapeutic effect.

As mentioned previously, a major problem in chemotherapy and gene therapy is the passive distribution of the therapeutic agent or therapeutic agent carriers which causes side effects, sometimes preventing the complete treatment protocol, and also reducing the drug efficiency since only part of the administered dose ends up at the target site. Targeted anticancer therapy is the most beneficial way to eliminate undesired side effects and improve the outcome of the therapy. Targeting nanoparticles to a specific cell line or tumor site can be achieved by conjugation of ligands specific to the receptors overexpressed in target cell lines or tumors. These ligands can be proteins (mainly antibodies and their fragments), peptides, nucleic acids (aptamers), small molecules, or others (vitamins or carbohydrates).

In a preferred embodiment of the invention, said therapeutic nanoparticle comprises SPION, natural AGO2 and an antibody specific to overexpressed cell surface receptors of cancer cell. At least in one embodiment this antibody is antiHer2 and the target is breast cancer so that the nanoparticles (SPION-AGO-antiHer) can be selectively delivered to tumor cells with overexpressed Her2 receptor. However, the person skilled in the art would appreciate that any antibody known in the art or a combination thereof may be used depending on the desired therapeutic effect and, for example the targeted tumor type.

SPIONs can be manipulated in a magnetic field and hence can be delivered magnetically to a site of interest. Hence, another aspect of the invention is to develop biocompatible gene delivery vehicles which comprise SPION, natural AGO2 and an antibody which can be localized at the tumor site synergistically via magnetic dragging and receptor targeting. In this manner, the invention utilizes two different targeting modalities: receptor mediated endocytosis and magnetic targeting which bring out a synergy for improved gene delivery systems.

In addition, AGO2 proteins conjugated to targeted therapeutic nanoparticles increase intracellular targeting of miRNA within the target cell, thus improving the efficacy of miRNA therapy.

Synthetic cationic polymers or other methods, such as those described in patent document WO 2015/138636, used in the art for the gene delivery lack imaging modality since they do not generate any form of detectable signal. Therefore, inorganic signal generating nanoparticles are conjugated with cationic polymers to allow tracking of these delivery vehicles via medical imaging devices. Two most widely used inorganic nanoparticles are SPIONs and luminescent semiconductor quantum dots which are trackable by MRI and microscopes/optical imaging instruments, respectively.

In an embodiment of the invention, said oligonucleotide carrier comprises natural AGO2 protein conjugated to a nanoparticle capable of generating a detectable signal. More specifically, said oligonucleotide carrier comprises a nanoparticle comprising AGO2 and SPION which is capable of generating a detectable signal by MRI. SPION-AGO2 nanoparticles benefit from the miRNA binding and delivery ability of AGO2 and the detectability by MRI. This allows determination of the biodistribution of particles by MRI and monitoring the outcome of therapy by MRI.

In an alternative embodiment of the invention, fluorescent dye is conjugated to the nanoparticle (SPION-AGO2-dye, SPION-AGO2-antiHer-DYE) which allows optical detection of nanoparticles in vitro and in vivo using microscopy techniques. In a preferred embodiment of the invention, the dye used is a far red fluorescent dye.

Recently, it was discovered that miRNAs play a significant role in efficacy of drugs by down-regulating genes that are important for drug function. The miRNA level of the tumor cells impacts the drug efficiency (Rukov et al. Brief Bioinform. 2013. 15:648-659). One object of the invention is to co-deliver miRNA and a chemotherapeutic agent to tumor tissue in order to enhance the drug efficiency. Studies conducted by the inventors of the present invention have demonstrated that the expression level of miRNAs of the MIR376 family is low in the breast cancer and transfection of MIR376A and MIR376B to breast cancer cells, i.e. MCF7, increased the therapeutic effect of cisplatin (Korkmaz et al. PLoS One. 2013. 8:e82556). In at least one embodiment of the invention, said miRNA is from the MIR376 family, the chemotherapeutic agent is Cisplatin and the target is breast tumor. However, the person skilled in the art would appreciate that any chemotherapeutic agent known in the art or a combination thereof may be used depending on the desired therapeutic effect.

Hyperthermia is a therapeutic procedure that promotes the increase of temperature in body tissues in order to change the function of the cellular structures. The rise in temperature interferes with the function of many enzymatic and structural proteins in the cells, and alters the cell growth and differentiation, which can induce apoptosis. It is also reported that some drugs perform better at higher temperatures than the body temperature. As a result, hyperthermia is being investigated as an adjuvant therapy to chemotherapy or radiotherapy. Preliminary studies have shown that superparamagnetic iron oxide nanoparticles (SPIONs) have appropriate intratumoral distribution and are able to promote controlled heating of the region to hyperthermic temperatures without causing major side effects (Silva et al. Int J Nanomedicine. 2011 6:591-603). In view of this, another embodiment of the present invention is directed to the development of biocompatible nanoparticles capable of delivering therapeutic cargo such as miRNA to a target cell line or tumor and produce hyperthermia as an adjuvant therapy.

The size and the charge of nanoparticles affect the biodistribution in vivo. For the molecular targeting of nanoparticles to tumor cells, the hydrodynamic size of the particles usually have to be smaller than 200 nm and preferably smaller than 150 nm, more preferably less than 100 nm and most preferably less than 50 nm. The preferred embodiments of the present invention are preferably small nanoparticles with a hydrodynamic size less than 200 nm, more preferably less than 150 nm, more preferably less than 100 nm and most preferably less than 50 nm.

The preferred embodiments of the present invention described in the examples below relate particularly to preparation of therapeutic nanoparticles comprising SPIONs covalently conjugated to AGO2 protein as gene carrier moiety and antiHer2 as targeting moiety for delivery of miRNA to Her2 overexpressing tumor cells in vitro or tumors in vivo. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

EXAMPLES

The following examples are provided to illustrate the present invention and are not intended to limit the scope of the invention.

Example 1: Preparation of AGO2 Conjugated SPIONs (SPION/AGO2)

In order to obtain water soluble and biocompatible SPIONs for miRNA delivery applications, SPION/PAA were synthesized directly using aqueous co-precipitation method with the incorporation of ferric and ferrous salts under alkaline conditions.

In detail, polyacrylic acid coated SPIONs (SPION/PAA) were synthesized in water with the precursors given molar ratio of $[PAA]:[Fe^{2+}]:[Fe^{3+}]:[OH^-]=3:2:1:6$ under argon atmosphere and at 85° C. for 1 h. Colloidal suspension was purified with ultracentrifugation using 10 kDa MWCO PES filter.

Figure 1:
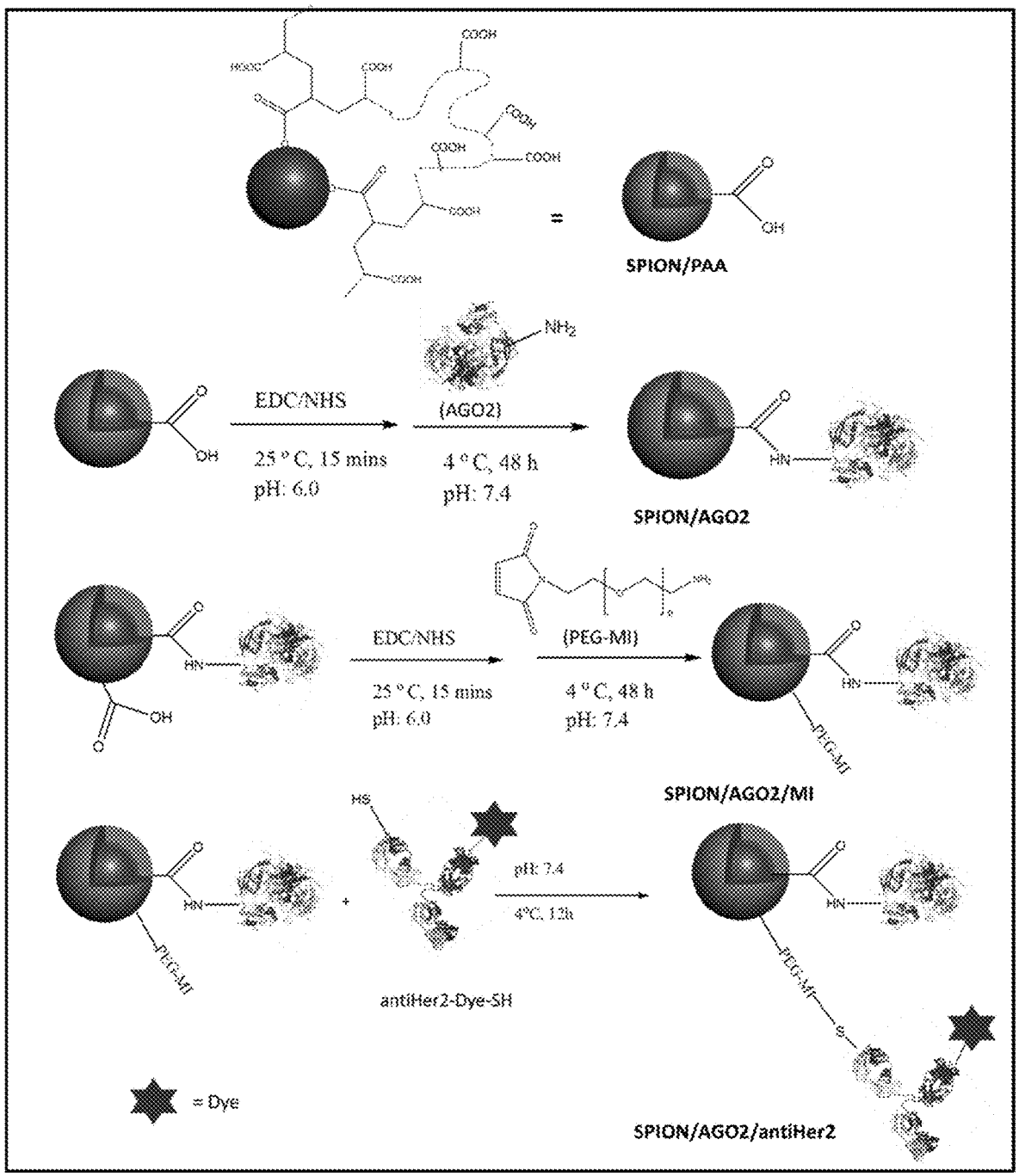
FIG. 1 demonstrates a schematic representation of SPION/AGO2/antiHer2 synthesis.

AGO2 protein was covalently attached to SPIONs via amide bond using the EDC/NHS chemistry between the carbonyl units of SPION/PAAs and primary amines of AGO2 (FIG. 1).

In detail, 50 mg of SPION/PAA was activated with 14 mg of EDC and 14.4 mg of sulfo-NHS in MES buffer at pH 6.0 at room temperature and then washed with PBS (pH 7.4) using 10 kDa MWCO ultracentrifuge tubes. 150 μg of AGO2 protein was added to activated SPIONs and mixed 48 h at +4° C. Reaction was quenched with excess hydroxylamine and SPION/AGO2 was purified with dialysis.

Bradford Assay, a method well-known in the art, was used to determine the amount of AGO2 on SPIONs. 5.5 μg AGO2 is present per mg of nanoparticles which corresponds to nearly 124 AGO2 per each nanoparticle.

Example 2: Preparation of antiHer2-Dye Conjugated SPIONs (SPION/AGO2/antiHer2-dye)

antiHer2 was conjugated to SPION surface with a PEG linker to prevent the shielding of antiHer2 by AGO2 protein and to improve the receptor-antibody interaction (FIG. 1). SPION/AGO2 was activated with EDC/sulfo NHS and purified using the method given for SPION/PAA/AGO2 synthesis, then 3 mg of $NH_2$-PEG-Mal (2000 Da) was added and mixed for 48 h at +4° C. and quenched with excess hydroxylamine. The product (SPION/AGO2-PEG-Mal) was purified using ultracentrifugation.

In order to track nanoparticles optically, a far red dye (DyLight 650) which would fluoresce at wavelengths where SPION/PAA have minimal absorption was conjugated to antibody and Dye-conjugated antibody was conjugated to SPION/AGO2 (FIGS. 1 and 2).

In order to obtain fluorescently tagged antiHer2, commercially available NHS active dye (Dylight 650®) was dissolved in DMF (10 mg/mL). antiHer2 antibody was dissolved in sodium borate buffer at pH=8.55. Antibody and dye solutions were mixed in the molar ratio of [antiHer2]:[Dye]=1:10 at room temperature for 1 h. Overall product was purified by dialysis. Protein concentration and molar ratio of protein and dye was calculated as antiHer2:Dye=1:0.8 by the following formulas:

$$\text{antiHer2 Concentration}(M) = \frac{[A280 - (A655 \times 0.037)] \times \text{dilution parameter}}{210{,}000 \times 0.1 \text{ cm}}$$

$$\text{Dylight 655 per mol antiHer2 (mol)} = \frac{A655 \times \text{dilution parameter}}{73{,}000 \times \text{protein concentration} \times 0.1 \text{ cm}}$$

antiHer2-Dye was mixed with Traut's Reagent at pH 8 with the molar ratio of [1:100] at room temperature for 2h, then the resulting product (antiHer2-dye-SH) was purified by dialysis.

Freshly prepared antiHer2-dye-SH was mixed with SPION/AGO2-PEG-Mal in PBS/EDTA at pH 7.2 and stirred for 1 h at room temperature and overnight at +4° C. Then, the overall product was purified by dialysis.

Example 3: Determination of antiHer2 Concentration on SPIONs

Mole number of DyLight 650® on SPIONs was calculated as 0.114 nmol based on the intensity of the dye emission at 672 nm (1.8 M (a.u.), dilution factor=20) and using the equation below.

PL intensity=$3.01 \times 10^8$[DyLight 650®]+$1.2 \times 10^5$

Since antiHer2: Dye ratio was 1:0.8, 0.142 nmol antiHer2 was attached to the nanoparticles. This is equal to 19 µg antiHer2/mL of SPION-AGO2/antiHer2-Dye (molecular weight of antiHer2=148,000 g/mol) (FIG. 3 and Table 1). Roughly, about 24 antiHer2 proteins were conjugated the surface of a single nanoparticle.

TABLE 1

Calculation of concentration of antiHer2 on SPIONs using PL intensity of DyLight 650 ®

| Dylight ® on SPIONs (nmol)[a] | Dylight ®:antiHer2 (molar ratio)[b] | antiHer2 on SPIONs (nmol) | antiHer2 per mg of particle (µg) |
|---|---|---|---|
| 0.114 | 0.8:1 | 0.142 | 24 |

[a]Calculated by the calibration curve of reference Dylight 650 ®
[b]Calculated by Beer-Lambert equation ($Abs_{protein}$ = 280 nm, $Abs_{Dylight}$ = 655 nm)

Example 4: Quantification of Number of AGO2 and antiHer2 per Nanoparticle

Number of proteins per nanoparticle was calculated using the following equation:

$$n = a \times N \times \frac{V}{\frac{4}{3}\pi r^3}$$

Where, a is the mole number of protein in 1 $cm^3$, N is Avogadro's number, V is the volume of nanoparticles in 1 $cm^3$ and r is the mean radius of nanoparticles (z-average hydrodynamic size). V is calculated by subtracting volume of water in 1 $cm^3$ dispersion from 1 $cm^3$. Volume of water in 1 $cm^3$ dispersion was also found over mass of water in 1 $cm^3$ dispersion.

$Mass_{water}$=$Mass_{liquid\ NPs}$−$Mass_{solid\ NPs}$

Example 5: Particle Properties

Hydrodynamic properties of SPIONs were measured after each conjugation step to monitor colloidal stability (Table 2).

TABLE 2

Change in hydrodynamic properties of SPIONs during functionalization steps

| Sample | HDR* Z-average (nm) | PDI | Zeta Potential (mV) | Medium |
|---|---|---|---|---|
| SPION/PAA | 14 | 0.40 | −19 | PBS |
| SPION/AGO2 | 20 | 0.43 | −23 | PBS |
| SPION/AGO2/PEG-MI | 30 | 0.59 | −21 | PBS |
| SPION/AGO2/antiHer2 | 49 | 0.23 | −24 | PBS |

*hydrodynamic size measured by dynamic light scattering

Figure 4:
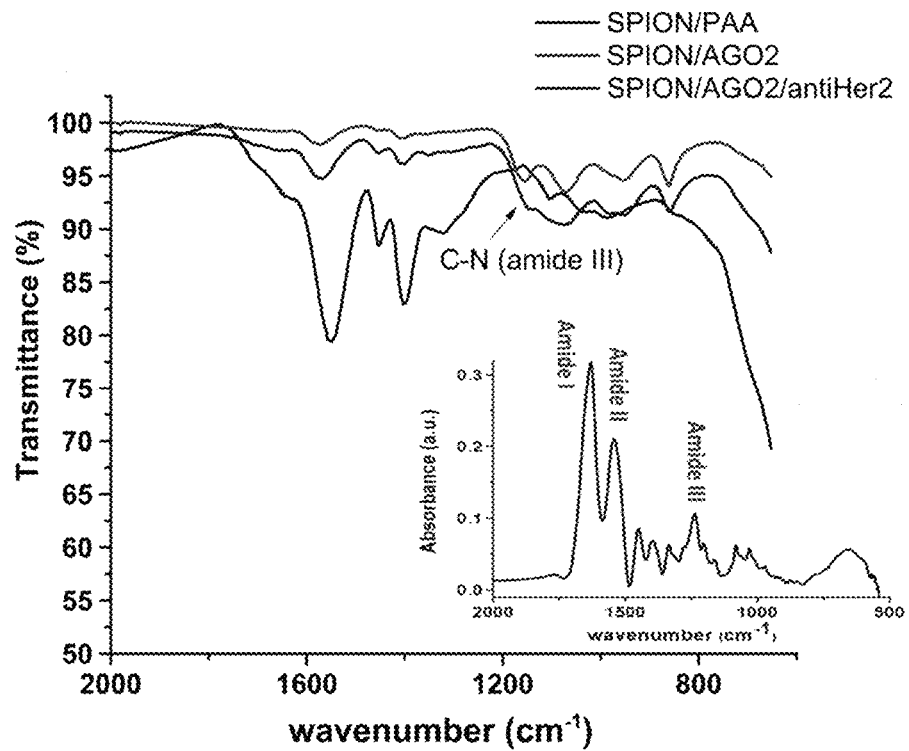
FIG. 4 demonstrates FTIR spectra of SPION/PAA, SPION/AGO2 and SPION/AGO2/antiHer2 (inset: FTIR spectrum of gelatin showing characteristic amide I, II, II IR bands of a protein).

For further confirmation of protein layers on SPIONs, comparative FTIR spectra of SPION/AGO2 and SPION/AGO2/antiHer2 were analyzed (FIG. 4). Proteins can be characterized through their typical IR bands in the mid IR region (amide A, B, I, II, III, IV) (Kong and Yu. Acta Biochim Biophys Sin. 2007. 39:549-559). Bands at 1150 $cm^{-1}$ on both spectra of SPION/AGO2 and SPION/AGO2/antiHer2 most probably indicates the C—N stretching (Amide III band) of proteins.

Example 6: Cytotoxicity of Nanoparticles

Figure 5:
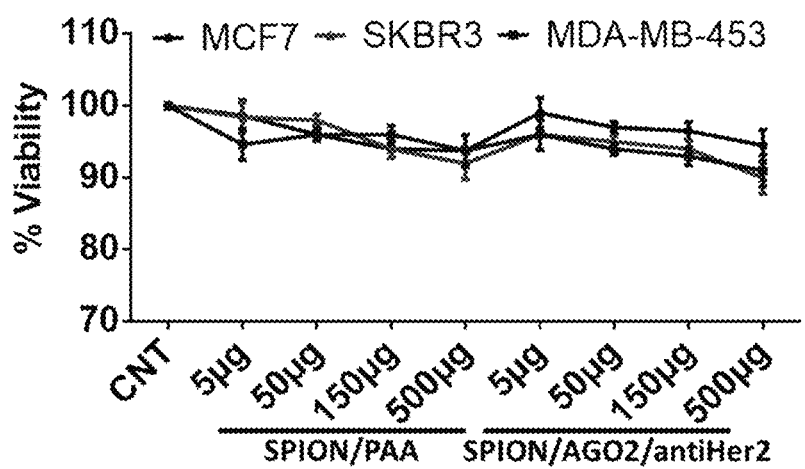
FIG. 5 demonstrates viability of cells exposed to SPION/PAA and SPION/AGO2/antiHer2 nanoparticles in a dose dependent manner. Viability of the cells was determined 48 hours after treatment.

A 3-(4,5-dimethylthiazol-2-yl)-2,5-diphenyl tetrazolium bromide (MTT) assay was performed to evaluate the influence of nanoparticles, SPION/PAA and SPION/AGO2/antiHer2, on cell viability. All cell lines showed more than 90% viability at all studied concentrations of both nanoparticles (FIG. 5).

Figure 6A:
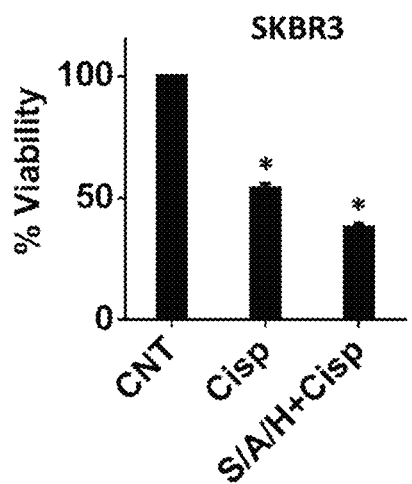
FIGS. 6A-B demonstrate viability of cells exposed to only cisplatin versus cisplatin with miRNA bound SPION/AGO2/antiHer2 (S/A/H) particles.
Figure 6B:
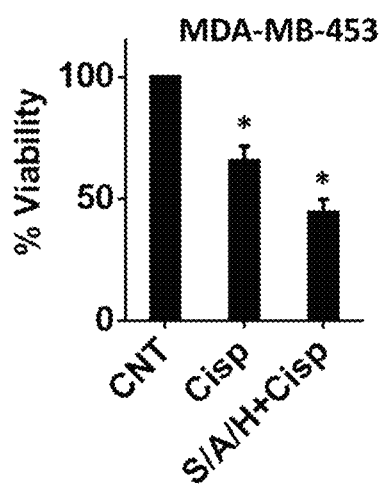

After determination of the non-toxic dose of nanoparticles, miRNA bound SPION/AGO2/antiHer2 nanoparticles were used in combination with cisplatin to increase toxicity of cisplatin. SKBR3 and MDA-MB-453 cells were treated with the 150 µg/ml nanoparticle and 5 µg/ml cisplatin at the same time for 48 hours. Viability was determined by MTT assay. Results indicated that cell viability is less than 50% when cisplatin is used in combination with miRNA bound SPION/AGO2/antiHer2 nanoparticles (FIG. 6).

Example 7: Determination of Targeting Ability of Nanoparticles in Vitro and in Vivo The Dylight 650® labelled nanoparticles were used for monitoring targeting specificity of nanoparticles for HER2 receptor overexpressing cells (MDA-MB-453 and SKBR3). MCF7 cells with low level of HER2 receptor on their cell surface were used as a control cell line for microscopy experiments. Cells were cultured on coverslides and treated with 150 µg of fluorescently labelled nanoparticles for indicated time periods, then fixed in ice-cold 4% paraformaldehyde/PBS. Following fixation, nuclei were stained using Hoechst (Invitrogen, 31716W) in PBS. Coverslides were mounted onto glass slides, and the fluorescent signal from samples was monitored using a confocal microscope (FIG. 8A).

Flow Cytometry analysis (FACS) also confirmed Her2 targeting of SPION/AGO2/antiHer2. MDA-MB-453 and SKBR3 were seeded onto a 12-well plate and treated with the nanoparticles for indicated times. The fluorescent positive cells were detected using BD FACSCanto™ instrument and analyzed using Flow Jo software (Tree Star Inc). Fluorescently labelled SPION/PAA particles were used as control (FIG. 8B).

In vivo targeting ability of the SPION/AGO2/antiHer2 nanoparticles was determined on nude mice. A xenograft mouse model was generated by subcutaneous injection of SKBR3 and MDA-MB-453 cells ($1\times10^7$ cells per mouse embedded in Matrigel (BD Biosciences)) in the right front flank of female nude mice (6-8 weeks, 20 g). When the tumors reached ~50-100 mm³, approximately 8-10 weeks after inoculation, the tumor bearing mice were injected via tail vein a single dose of nanoparticles (10 mg/kg Fe). Fe concentration of the injected solution was calculated by inductively coupled plasma. After 24 hours of injection, in vivo imaging of the nanoparticles was conducted under isoflurane inhalation anesthesia by using IVIS Spectrum imaging system (Caliper Life Sciences) with the Living Image software package (FIG. 8C). Images indicate localization of SPION/AGO2/antiHer2 nanoparticles in the tumor site.

Example 8: Determination of miRNA Delivering Capacity of SPION/AGO2/antiHer2 Nanoparticles SPION/AGO2/antiHer2 nanoparticles were incubated in RNA binding buffer (100 mM KCl, 2 nM $MgCl_2$, 10 mM Tris-HCl in DEPC water) together with 20 nM miR376b mimics (Dharmacon) at 4° C. for 2 hours on rotator. 10 µg protein extract was added in RBB buffer before incubation of nanoparticles with miRNA mimics to use the ability of endogenous RNA-induced silencing complex (RISC) elements to bind miRNA to AGO2 protein. SKBR3 and MDA-MB-453 cells were treated with miRNA-bound SPION/AGO2/antiHer2 nanoparticles and change in level of miR376b and its targets (ATG4C and BECN1) were determined by RT-PCR (FIG. 9A). AntiHer2 conjugated SPION nanoparticles (SPION/antiHer2) which lack miRNA binding AGO2 were used as control. Changes in protein level of miR376b targets were determined by immunoblotting assay (FIG. 9B).

For RT-PCR, total RNA was extracted using TRIzol reagent (Sigma-Aldrich, #T9424) according to the manufacturer's instructions. cDNA was reverse transcribed from DNase-treated total RNA using M-MuLV reverse transcriptase (Fermentas, #EP0351), random hexamers (Invitrogen, #48190-011) and miR376b stem-loop primer.

For single step qRT-PCR reaction, SYBR Green Quantitative RT-PCR kit (Roche, #04-913-914-001) and a LightCycler 480 (Roche) were used. To activate the SYBR green, an initial cycle of 95° C., 10 min was performed followed by PCR reactions: 40 cycles of 95° C. for 15 s and 60° C. for 1 min. Then a thermal denaturation protocol was used to generate the dissociation curves for the verification of amplification specificity (a single cycle of 95° C. for 60 s, 55° C. for 60 s and 80 cycles of 55° C. for 10 s). Changes in mRNA and miRNA levels were quantified using the $2^{-\Delta\Delta CT}$ method using GAPDH (glyceraldehyde-3-phosphate dehydrogenase) mRNA and U6 small nuclear 1 (RNU6-1) mRNA as control. Primers used during the study were: BECN1 primers 5'-AGGTTGAGAAAGGCGAGACA-3' (SEQ ID NO: 1); 5'-GCTTTTGTCCACTGCTCCTC-3' (SEQ ID NO: 2); ATG4C primers 5'-GCATAAAGGATTTCCCTCTTGA-3' (SEQ ID NO: 3); 5'-GCTGGGATCCATTTTTCG-3' (SEQ ID NO: 4), and GAPDH primers 5'-AGCCACATCGCTCAGACAC-3' (SEQ ID NO: 5); 5'-GCCCAATACGAC-CAAATCC-3' (SEQ ID NO: 6).

TaqMan qRT-PCR reactions were performed using FastStart Universal Probe Master kit (ROCHE, #04913957001) and LightCycler 480 (Roche) according to the protocols described previously. Primers and the probe used during the study were: Stem-loop primer, 5'-GTCGTATCCAGTGCAGGGTCCGAGGTAT-TCGCACTGGATACGACAACATGG-3' (SEQ ID NO: 7); Forward primer, 5'-GTTAATCATAGAGGAAAAT-3' (SEQ ID NO: 8); Reverse primer, 5'-GTGCAGGGTCCGAGGT-3' (SEQ ID NO: 9); TaqMan Probe, 5'(6-FAM)-GCA GGG GCC ATG CTA ATC TTC TCT GTA TCG -(TAMRA-sp)3' (SEQ ID NO: 10); U6 forward primer, 5'-CTCGCTTCGGCAGCACA-3' (SEQ ID NO: 11); U6 reverse primer, 5'-RAACGCTTCACGAATTTGCGT-3' (SEQ ID NO: 12); U6 TaqMan Probe 5'(6-FAM)-GCA GGG GCC ATG CTA ATC TTC TCT GTA TCG-(TAMRA-Sp)3' (SEQ ID NO: 10).

For immunoblotting assays, cells were lysed at indicated time points in RIPA buffer (50 mM TRIS-HCl pH 7.4, 150 mM NaCl, 1% NP40, 0.25% Na-deoxycholate) supplemented with a complete protease inhibitor cocktail (Roche, 04-693-131-001) and 1 mM phenylmethylsulfonyl fluoride (PMSF, Sigma-Aldrich, P7626). Changes in the protein level were determined by western blotting with specific antibodies (anti-BECN1 (Santa Cruz, sc-11427), anti-ATG4C (Sigma-Aldrich, AB75056), and anti-β-ACTIN (Sigma-Aldrich, A5441) antibody as loading control). Band intensities were quantified using the ImageJ software.

Example 9: Magnetic Hyperthermia

Figure 7:
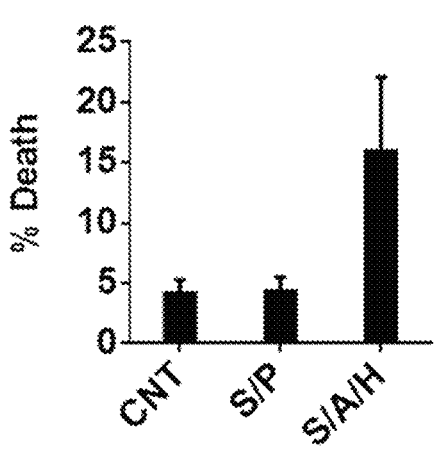
FIG. 7 demonstrates viability of cells treated with SPION/PAA (S/P) and SPION/AGO2/antiHer2 (S/A/H) under magnetic field. Hyperthermia induced cell death was determined with standard Trypan Blue assay.

SKBR3 cells were seeded onto 11 mm plates and treated with 150 µg/ml SPION/PAA and SPION/AGO2/antiHer2 nanoparticles. SPION/PAA particles were used as control. After 12 hours of the treatment, cells were exposed to magnetic field (400 kHz, 5 A) for 5 minutes. Then, heated cells were incubated in a 5% $CO_2$ humidified incubator at 37° C. for 24 hours. Cell viability was determined with standard Trypan Blue assay at the end of incubation and indicated about 3 fold higher cell death in magnetic hyperthermia conditions (FIG. 7).

In a nutshell, the present invention proposes an oligonucleotide carrier, wherein said oligonucleotide carrier comprises a pharmaceutically acceptable nanoparticle and wherein said pharmaceutically acceptable nanoparticle is bound to at least one Argonaute protein or a variant thereof.

In a further aspect of the present invention said pharmaceutically acceptable nanoparticle is selected from a group comprising lipid nanoparticles, polymeric nanoparticles, inorganic particles such as magnetic nanoparticles, quantum dots, gold nanoparticles, silver nanoparticles, silica nanoparticles, carbon dots and graphene.

In a further aspect of the present invention, said pharmaceutically acceptable nanoparticle is a magnetic nanoparticle.

In a further aspect of the present invention, said pharmaceutically acceptable nanoparticle is a superparamagnetic iron oxide nanoparticle.

In a further aspect of the present invention, said nanoparticle is bound to at least one Argonaute protein or a variant thereof by a covalent bond.

In a further aspect of the present invention, said Argonaute protein or a variant thereof is an Argonaute-2 protein or a variant thereof.

In a further aspect of the present invention, said oligonucleotide carrier further comprises at least one targeting moiety selected from proteins, peptides, nucleic acids, small molecules, vitamins and carbohydrates.

In a further aspect of the present invention, said pharmaceutical nanoparticle is bound to at least one targeting moiety.

In a further aspect of the present invention, said targeting moiety is an antibody.

In a further aspect of the present invention, said targeting moiety is an antibody specific for anti-Her2/NEU receptor.

In a further aspect of the present invention, said targeting moiety is antiHer2.

In a further aspect of the present invention, said oligonucleotide carrier further comprises at least one fluorescent dye moiety.

In a further aspect of the present invention, said oligonucleotide carrier further comprises at least one oligonucleotide bound to Argonaute protein or a variant thereof.

In a further aspect of the present invention, said oligonucleotide is RNA.

In a further aspect of the present invention, said oligonucleotide is miRNA.

In a further aspect of the present invention, said miRNA is chosen from the MIR376 family.

In a further aspect of the present invention, said oligonucleotide carrier further comprises at least one chemotherapeutic agent moiety.

In a further aspect of the present invention, said chemotherapeutic agent is a Platinum compound.

In a further aspect of the present invention, said chemotherapeutic agent is Cisplatin.

In a further aspect of the present invention, the size of said oligonucleotide carrier is below 150 nm.

In a further aspect, the present invention proposes an oligonucleotide carrier as described above for use as a medicament.

In a further aspect, the present invention proposes an oligonucleotide carrier as described above for use as a medicament in the treatment of cancer.

In a still further aspect, the present invention proposes a pharmaceutical composition comprising the oligonucleotide carrier as above and a chemotherapeutic agent.

In a further aspect, the present invention proposes a pharmaceutical composition as described above for use as a medicament.

In a further aspect, the present invention proposes a pharmaceutical composition as described above for use as a medicament in the treatment of cancer.

In a further aspect, the present invention proposes a method of inducing hyperthermia in a cell comprising the steps of:

a) contacting the cell with a therapeutically effective amount of the oligonucleotide carrier as described above or the pharmaceutical composition as described above, wherein said pharmaceutically acceptable nanoparticle is a superparamagnetic iron oxide nanoparticle, b) exposing the cell to a magnetic field.

In a further aspect, the present invention proposes a method of inhibiting or reducing the expression of a target gene in a cell comprising contacting the cell with a therapeutically effective amount of the oligonucleotide carrier as described above or the pharmaceutical composition as described above.

In a further aspect of the present invention, said pharmaceutically acceptable nanoparticle is a superparamagnetic iron oxide nanoparticle and said targeting moiety is anti-Her2.

In a further aspect of the present invention, said pharmaceutically acceptable nanoparticle is a superparamagnetic iron oxide nanoparticle, said targeting moiety is antiHer2, said oligonucleotide is chosen from the MIR376 family and said chemotherapeutic agent is Cisplatin.

What is claimed is:

1. An anionic oligonucleotide carrier for delivering an oligonucleotide to a cell, wherein the oligonucleotide carrier comprises:
   a pharmaceutically acceptable anionic nanoparticle covalently bound to at least one Argonaute protein or a variant thereof, wherein
   the pharmaceutically acceptable anionic nanoparticle is selected from a group consisting of superparamagnetic iron oxide nanoparticles and quantum dots.

2. The oligonucleotide carrier according to claim 1, wherein the Argonaute protein or the variant thereof is an Argonaute-2 protein or a variant thereof.

3. The oligonucleotide carrier according to claim 1, wherein the oligonucleotide carrier further comprises at least one targeting moiety selected from proteins, peptides, nucleic acids, small molecules, vitamins and carbohydrates.

4. The oligonucleotide carrier according to claim 3, wherein the pharmaceutically acceptable nanoparticle is bound to at least one of the targeting moiety.

5. The oligonucleotide carrier according to claim 4, wherein the targeting moiety is an antibody.

6. The oligonucleotide carrier according to claim 5, wherein the targeting moiety is an antibody that binds Her2/NEU receptor.

7. The oligonucleotide carrier according to claim 6, wherein the antibody that binds Her2/NEU receptor is antiHer2.

8. The oligonucleotide carrier according to claim 1, wherein the oligonucleotide carrier further comprises at least one fluorescent dye moiety.

9. The oligonucleotide carrier according to claim 1, wherein the oligonucleotide carrier further comprises at least one oligonucleotide bound to the Argonaute protein or the variant thereof.

10. The oligonucleotide carrier according to claim 9, wherein the oligonucleotide is RNA.

11. The oligonucleotide carrier according to claim 10, wherein the oligonucleotide is miRNA.

12. The oligonucleotide carrier according to claim 11, wherein the miRNA is chosen from MIR376 family.

13. The oligonucleotide carrier according to claim 12, wherein the pharmaceutically acceptable nanoparticle is a superparamagnetic iron oxide nanoparticle, the pharmaceutically acceptable nanoparticle is bound to a targeting moiety that is an antibody that binds Her2/NEU receptor, and the antibody that binds Her2/NEU receptor is antiHer2.

14. A medicament comprising the oligonucleotide carrier according to claim 9.

15. A medicament for the treatment of cancer comprising the oligonucleotide carrier according to claim 9.

16. A pharmaceutical composition, comprising the oligonucleotide carrier according to claim 9 and a chemotherapeutic agent.

17. The pharmaceutical composition according to claim 16, wherein the pharmaceutically acceptable nanoparticle is a superparamagnetic iron oxide nanoparticle, the pharmaceutically acceptable nanoparticle is bound to a targeting moiety that is an antibody that binds Her2/NEU receptor, the antibody that binds Her2/NEU receptor is antiHer2, the oligonucleotide is chosen from MIR376 family and the chemotherapeutic agent is Cisplatin.

18. A method of inducing hyperthermia in a cell comprising the steps of
a) contacting the cell with a therapeutically effective amount of the oligonucleotide carrier according to claim 9, wherein the pharmaceutically acceptable nanoparticle is a superparamagnetic iron oxide nanoparticle, and
b) exposing the cell to a magnetic field.

19. A method of inhibiting or reducing expression of a target gene in a cell, comprising contacting the cell with a therapeutically effective amount of the oligonucleotide carrier according to claim 9.

20. The oligonucleotide carrier according to claim 1, wherein the oligonucleotide carrier further comprises at least one chemotherapeutic agent moiety.

21. The oligonucleotide carrier according to claim 20, wherein the chemotherapeutic agent is a Platinum compound.

22. The oligonucleotide carrier according to claim 21, wherein the chemotherapeutic agent is Cisplatin.

23. The oligonucleotide carrier according to claim 1, wherein the size of the oligonucleotide carrier is below 150 nm.

24. The anionic oligonucleotide carrier for delivering an oligonucleotide to a cell according to claim 1, wherein the pharmaceutically acceptable anionic nanoparticle comprises a polyacrylic acid (PAA) coating.

25. The anionic oligonucleotide carrier for delivering an oligonucleotide to a cell according to claim 1, wherein the pharmaceutically acceptable anionic nanoparticle comprises a polyacrylic acid coated superparamagnetic iron oxide nanoparticle (SPION/PAA), and the SPION/PAA is anionic in aqueous media.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: BECN1 primer for the single step qRT-PCR
      reaction

<400> SEQUENCE: 1
aggttgagaa aggcgagaca                                              20

<210> SEQ ID NO 2
<211> LENGTH: 20
<212> TYPE: DNA
<213> ORGANISM: Artificial Sequence
<220> FEATURE:
<223> OTHER INFORMATION: BECN1 primer for the single step qRT-PCR
      reaction

<400> SEQUENCE: 2
gcttttgtcc actgctcctc                                              20

<210> SEQ ID NO 3
<211> LENGTH: 22
<212> TYPE: DNA
<213> ORGANISM: Artificial Sequence
<220> FEATURE:
<223> OTHER INFORMATION: ATG4C primer for the single step qRT-PCR
      reaction -continued

<400> SEQUENCE: 3
gcataaagga tttccctctt ga					22

<210> SEQ ID NO 4
<211> LENGTH: 18
<212> TYPE: DNA
<213> ORGANISM: Artificial Sequence
<220> FEATURE:
<223> OTHER INFORMATION: ATG4C primer for the single step qRT-PCR
      reaction

<400> SEQUENCE: 4
gctgggatcc atttttcg					18

<210> SEQ ID NO 5
<211> LENGTH: 19
<212> TYPE: DNA
<213> ORGANISM: Artificial Sequence
<220> FEATURE:
<223> OTHER INFORMATION: GAPDH primer for the single step qRT-PCR
      reaction

<400> SEQUENCE: 5
agccacatcg ctcagacac					19

<210> SEQ ID NO 6
<211> LENGTH: 19
<212> TYPE: DNA
<213> ORGANISM: Artificial Sequence
<220> FEATURE:
<223> OTHER INFORMATION: GAPDH primer for the single step qRT-PCR
      reaction

<400> SEQUENCE: 6
gcccaatacg accaaatcc					19

<210> SEQ ID NO 7
<211> LENGTH: 51
<212> TYPE: DNA
<213> ORGANISM: Artificial Sequence
<220> FEATURE:
<223> OTHER INFORMATION: Stem-loop primer for the TaqMan qRT-PCR
      reactions

<400> SEQUENCE: 7
gtcgtatcca gtgcagggtc cgaggtattc gcactggata cgacaacatg g					51

<210> SEQ ID NO 8
<211> LENGTH: 19
<212> TYPE: DNA
<213> ORGANISM: Artificial Sequence
<220> FEATURE:
<223> OTHER INFORMATION: Forward primer for the TaqMan qRT-PCR reactions

<400> SEQUENCE: 8
gttaatcata gaggaaaat					19

<210> SEQ ID NO 9
<211> LENGTH: 16
<212> TYPE: DNA
<213> ORGANISM: Artificial Sequence
<220> FEATURE:
<223> OTHER INFORMATION: Reverse primer for the TaqMan qRT-PCR reactions

<400> SEQUENCE: 9
gtgcagggtc cgaggt					16

```
<210> SEQ ID NO 10
<211> LENGTH: 30
<212> TYPE: DNA
<213> ORGANISM: Artificial Sequence
<220> FEATURE:
<223> OTHER INFORMATION: TaqMan Probe and U6 TaqMan Probe for the TaqMan
      qRT-PCR reactions
<220> FEATURE:
<221> NAME/KEY: misc_feature
<222> LOCATION: (1)..(1)
<223> OTHER INFORMATION: g is attached to 6-FAM
<220> FEATURE:
<221> NAME/KEY: misc_feature
<222> LOCATION: (30)..(30)
<223> OTHER INFORMATION: g is attached to TAMRA-sp

<400> SEQUENCE: 10 gcagggcca tgctaatctt ctctgtatcg                                          30

<210> SEQ ID NO 11
<211> LENGTH: 17
<212> TYPE: DNA
<213> ORGANISM: Artificial Sequence
<220> FEATURE:
<223> OTHER INFORMATION: U6 forward primer for the TaqMan qRT-PCR
      reactions

<400> SEQUENCE: 11
ctcgcttcgg cagcaca                                                       17

<210> SEQ ID NO 12
<211> LENGTH: 20
<212> TYPE: DNA
<213> ORGANISM: Artificial Sequence
<220> FEATURE:
<223> OTHER INFORMATION: U6 reverse primer for the TaqMan qRT-PCR
      reactions

<400> SEQUENCE: 12
aacgcttcac gaatttgcgt                                                    20
```